United States Patent
Myhrberg et al.

(10) Patent No.: US 7,597,683 B2
(45) Date of Patent: Oct. 6, 2009

(54) STERILE SYRINGE

(75) Inventors: Lennart Myhrberg, Älvängen (SE); Håkan Samuelsson, Onsala (SE)

(73) Assignee: Millipore AB, Nodinge (SE)

( * ) Notice: Subject to any disclaimer, the term of this patent is extended or adjusted under 35 U.S.C. 154(b) by 405 days.

(21) Appl. No.: 11/359,482

(22) Filed: Feb. 23, 2006

(65) Prior Publication Data

US 2006/0211995 A1    Sep. 21, 2006

(30) Foreign Application Priority Data

Mar. 4, 2005    (SE) .................................. 0500507

(51) Int. Cl.
    *A61M 5/00*    (2006.01)
(52) U.S. Cl. ..................................... 604/187
(58) Field of Classification Search ................ 604/187, 604/110, 227, 214, 264, 107, 199, 218, 221, 604/220, 224, 141, 212, 216
    See application file for complete search history.

(56) References Cited

U.S. PATENT DOCUMENTS

| | | | |
|---|---|---|---|
| 3,885,710 A * | 5/1975 | Cohen | 222/129 |
| 3,902,491 A | 9/1975 | Lajus | |
| 4,511,534 A | 4/1985 | Bennett, Jr. et al. | |
| 4,713,060 A | 12/1987 | Riuli | |
| 5,324,266 A | 6/1994 | Ambrisco et al. | |
| 6,056,724 A | 5/2000 | Lacroix | |
| 6,258,062 B1 * | 7/2001 | Thielen et al. | 604/141 |
| 2001/0018575 A1 | 8/2001 | Lyza, Jr. | |
| 2003/0065291 A1 | 4/2003 | Corrigan | |
| 2003/0187388 A1 | 10/2003 | Sharon et al. | |

FOREIGN PATENT DOCUMENTS

| | | |
|---|---|---|
| DE | 199 25 621 | 12/1999 |
| DE | 19925621 A1 * | 12/1999 |
| EP | 0 743 072 | 11/1996 |
| EP | 1 459 775 | 9/2004 |
| JP | 31361 | 6/1917 |
| JP | 58-223735 | 12/1983 |
| JP | 62-299270 | 12/1987 |
| JP | 4045856 | 2/1992 |
| JP | 09-313606 | 12/1997 |
| JP | 2000-316973 | 11/2000 |
| WO | WO 97/44076 | 11/1997 |

OTHER PUBLICATIONS

Translation of Notice of Rejection for JP application No. 2006-039279.

* cited by examiner

*Primary Examiner*—Manuel A Mendez
(74) *Attorney, Agent, or Firm*—Dickstein Shapiro LLP

(57) ABSTRACT

A syringe for a fluid comprises a cylinder, a piston portion arranged in the cylinder and slidable on its inside, and an operating means connected to the piston portion for sliding thereof. The operating means projects from a first end of the cylinder and the cylinder has at a second end an inlet and outlet part for said fluid. Moreover a sealing means is connected in a contamination-free manner to the cylinder in the area of the first end thereof and extends into the cylinder to isolate, sealed against contamination, the inside of the cylinder from the environment.

20 Claims, 5 Drawing Sheets

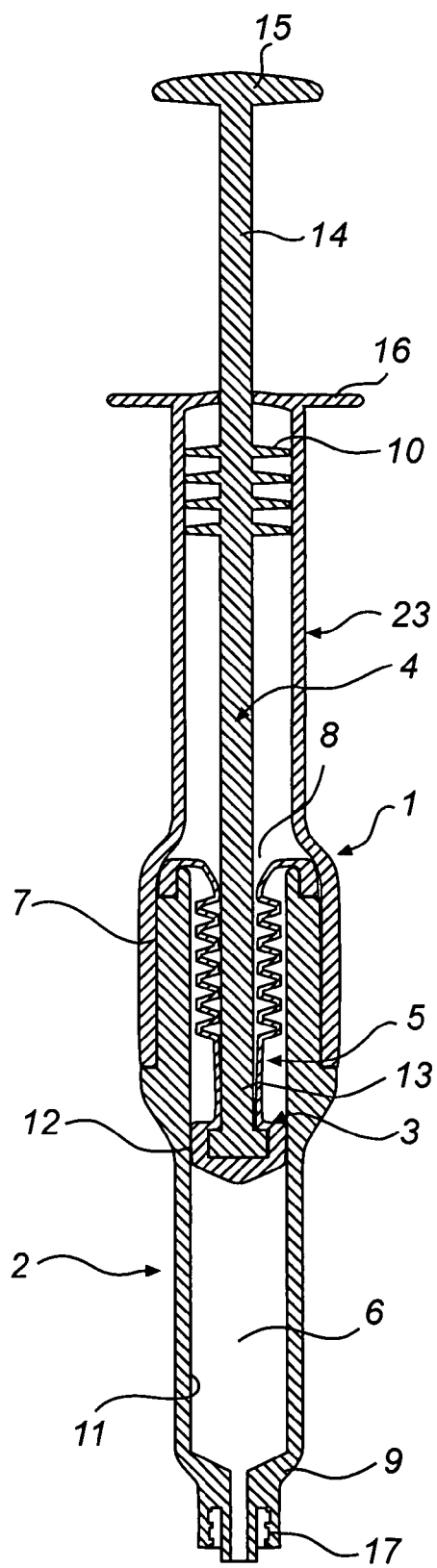
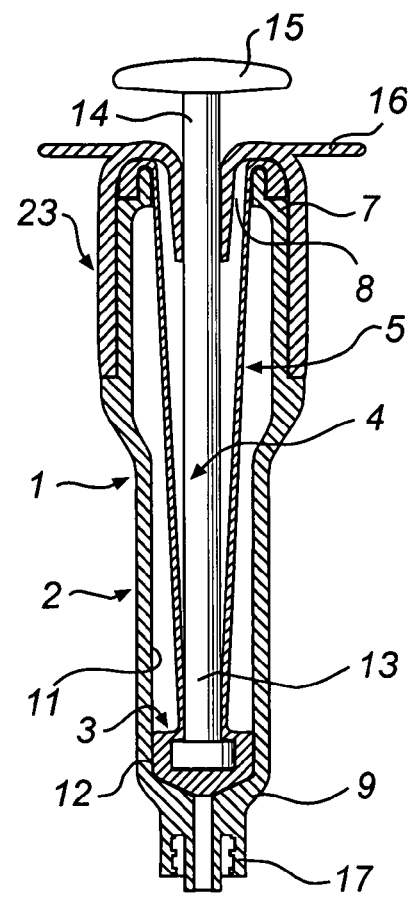
Fig. 5
Fig. 6

STERILE SYRINGE

CROSS-REFERENCE TO RELATED APPLICATIONS

This application claims priority to Sweden Patent Application No. 0500507-9, filed on Mar. 4, 2005, the entire contents of which are hereby incorporated by reference.

FIELD OF THE INVENTION

The present invention relates generally to a syringe for fluid, preferably a liquid medium, with a cylinder, a piston portion which is arranged in the cylinder and slidable on its inside, and an operating means connected to the piston portion for sliding thereof. The operating means projects from a first end of the cylinder and the cylinder has at a second end an inlet and outlet part for the fluid.

More specifically, the present invention relates to a syringe for taking up and discharging a fluid, said syringe having on the one hand a cylinder for taking up, for instance, a liquid medium, the cylinder having a first end with an opening and a second end with an inlet and outlet part, and, on the other hand, a sealingly guided piston portion which is movable back and forth inside the cylinder between its first and second ends, said piston portion being actuated by the operating means which projects from the opening at the first end of the cylinder to be, in turn, actuatable from the outside for moving the piston portion back and forth in the cylinder.

BACKGROUND ART

A syringe of the above type can be used in a variety of fields, for instance as sampling or injection syringe in the medical field.

An application which in this case is particularly preferred but not limiting is, for instance, in the pharmaceutical and biotechnology field and to some extent also in fields such as foods and cosmetics. In these fields there is a need for routine sampling and analysis of different media, for instance for microbiological control, cell counting or, where appropriate, chemical analyses, or supply of regulating or active media in certain process steps in manufacture of products in the fields in question.

In such manufacture involving stringent requirements as to no contamination, or minor contamination, of the media included in the process, manufacture normally takes place in a closed process vessel. There is, however, a risk of contamination when one or more media are to be supplied to the process vessel or a sample is to be taken from the process vessel. Due to this risk of contamination in and around the process vessel, the supply and sampling of the media therefore take place in clean room environment, which requires great investments, expensive equipment and acceptable working conditions for the staff.

The syringe according to the present invention is in the first place, but not exclusively, intended to be used in contamination-free take-up from a process vessel to a collecting vessel or the like. The syringe can be used to transfer fluid from a collecting vessel and supply the fluid to a process vessel or vice versa. The syringe can also be arranged for other dosing, transport or sampling, such as transfer of the fluid to a laboratory for analysis etc.

In sampling according to prior-art technique, there are problems with false positive results, that is that the medium from which samples are taken is not contaminated but the sample nevertheless indicates contamination. This is a costly problem since the medium that is being sampled is often expensive and occurs in large volumes. False positive results are often due to problems with the sampling equipment which may cause contamination of the sample.

In prior-art syringes it has been found that the piston portion, in spite of its sealing engagement with the inside of the cylinder by means of a seal, in the form of at least one, but usually two sealing rings/flanges, by definition is not perfectly sealed against the inside of the cylinder.

When the piston portion initially, by the operating means, is moved upwards in the cylinder from a lower starting position to an upper "turning position" to take up/suck in medium from a collecting vessel, microorganisms and other very small contaminants, which after breaking of the sterile package or in some other manner get stuck on the syringe and then also on the inside of the cylinder, can pass the seal and enter the space on the fluid side of the piston portion where the contaminants mix with the sucked-in medium and contaminate it.

When the piston portion then, by the operating means, which can be a piston rod, is again moved inwards in the cylinder from the turning position to the starting position to discharge the medium to be added, analysed etc, the contaminants accompany the medium out of the syringe. This can wholly or partly destroy or damage the medium and make it difficult, or impossible, for the medium to be used, analysed etc. Owing to the contamination, the medium can alternately, or in addition, be dangerous to use.

It has also been found that as the piston portion moves inwards in the cylinder there easily forms, despite the seal, a very thin film of the received medium on the inside of the cylinder, that is on the piston portion side opposite to the fluid side. If the medium has a strong odour, the user clearly notices this around the syringe. If the medium is injurious to health or dangerous to the environment or even poisonous, the forming of film may constitute a serious health or environmental hazard. Furthermore this film can additionally increase the risk that contaminants get stuck on the inside of the cylinder, and in the cases where the syringe is used several times before being finally discarded or cleaned for reuse, the risk also increases that the medium in the syringe should be contaminated by contaminants or microorganisms more easily getting stuck on the film formed.

An additional risk of prior-art syringes is that the contamination guard, for instance the protective bellows, is positioned so that it risks being damaged in the handling of the syringe. If a hole occurs in the contamination guard, there is a risk that contaminants enter the syringe and contaminate the medium in the cylinder of the syringe.

SUMMARY OF THE INVENTION

An object of the present invention is to provide a syringe of the type stated by way of introduction, which eliminates one of the above drawbacks and risks in a simple and effective manner.

Another object of the invention is to provide such a syringe, which thus is contamination-sealed in the sense that exterior microorganisms or other contaminants cannot mix with the medium received in the syringe and contaminate this.

Yet another object of the invention is to provide such a syringe in which current requirements as to contamination-free transfer of the medium involved all the way from the process vessel to adding and/or analysing etc. through the syringe are satisfied.

A further object of the invention is to provide a syringe which is inexpensive and simple to manufacture.

The above objects and other objects that will be evident from the following description are achieved by a device according to the appended claims.

According to one aspect of the present invention, a syringe for fluid is provided, comprising a cylinder, a piston portion which is arranged in the cylinder and slidable on its inside, and an operating means connected to the piston portion for sliding thereof. The operating means projects from a first end of the cylinder and the cylinder has at a second end an inlet and outlet part for said fluid. A sealing means is connected in a contamination-free manner to the cylinder in the area of its first end and extends into the cylinder to isolate, sealed against contamination, the inside of the cylinder from the environment. In one embodiment, the sealing means is at least connected in a contamination-free manner to the cylinder and extends into the cylinder to isolate, sealed against contamination, the inside of the cylinder from the operating means which can be, for instance, a piston rod. The syringe is preferably intended for sampling of liquids, but of course the present invention can be used in other applications and also for other media, such as gases. The sealing means protects the inside of the cylinder from the environment and the risk of contamination. This is ensured by the sealing means separating the piston rod from the inside of the cylinder, thus forming a chamber isolated from the environment and defined by the cylinder, the sealing means and a piston portion at the inner end of the piston rod. This isolated chamber is presterilised simultaneously with the syringe, after which the chamber remains free of contaminants from the environment outside the syringe.

Preferably said sealing means is arranged to seal between the inside of the cylinder and an inner end of the operating means extending into the cylinder. This is ensured by the sealing means extending from sealed connection to the edge of the first end of the cylinder to sealed connection to the inner end of the operating means. This sealing effect can be provided at the inner end of the operating means in various ways, for instance by the end being circumferentially isolated from the cylinder by the sealing means.

Preferably, said sealing means is located substantially inside the cylinder. When the operating means is in its retracted position, the entire sealing means is positioned inside the cylinder except for the part of the inner end of the sealing means which is attached to the second end of the cylinder. When the operating means is in its extracted position, the sealing means can be designed to accompany, partially folded in two, the operating means out of the opening of the cylinder.

The sealing means preferably has an open end into which the inner end of the operating means extends. It is also conceivable for the inner end of the sealing means to be provided with an opening, which requires a piston portion or the like to seal between the inner end of the operating means and the inside of the cylinder.

Preferably the open end of the sealing means is connected to the first end of the cylinder. This can be ensured in various ways, for instance by the elastic sealing means being "turned inside out" around the edge of the second end of the cylinder, or alternatively the sealing means being locked in a form-fitting manner by means of a sleeve at the second end of the cylinder.

Preferably a guide sleeve is arranged at the first end of the cylinder to guide the operating means. This guide sleeve cooperates with the operating means. Cooperation between the guide sleeve and the operating means is achieved either by flanges of the piston rod which extend radially out from the piston rod to abut against the guide sleeve as shown in FIGS. 1-5 and 7, or by the guide sleeve having a portion extending inwards to the operating means as shown in FIG. 6.

Preferably the sealing means forms, at its end opposite to the open end, a piston-like portion, which is movable by the operating means inside the cylinder, said piston-like portion sealingly engaging the inside of the cylinder, a corresponding embodiment being shown in FIG. 7. When the operating means is moved in a direction out of the cylinder, the sealing means is deformed, which deformation can be taken up in different ways. In one alternative, the sealing means is formed like a bellows so that the bellows folds during said movement of the operating means as shown in FIG. 5; in another alternative the sealing means is flat and accompanies, folded in two, the operating means out of the first end of the cylinder during said movement of the operating means.

Preferably the open end of the sealing means is connected to the first end of the cylinder by being turned inside out around the edge of the first end of the cylinder.

Preferably the sealing means is made of an elastic and sealing material in order to exclude contaminants from the fluid that is being handled by the syringe.

Preferably the syringe and the sealing means are presterilised, preferably by irradiation, autoclaving or some other appropriate method, whereby the syringe is kept sterile, above all on the inside, up to the occasion of use.

Preferably the second end of the sealing means, at the opposite end of the operating means, is movable and the inner end of the sealing means is held still at the first end of the cylinder. In this way, a deformation of the sealing means is provided while at the same time fluid is sucked into the chamber of the syringe.

BRIEF DESCRIPTION OF THE DRAWINGS

The invention will now be described in more detail with reference to the accompanying drawings, in which FIG. 5 is a section of an embodiment of the syringe in a second starting position with a bellows-type sealing means, FIG. 6 is a section of an embodiment of the syringe with a supporting sleeve for the piston rod.

DETAILED DESCRIPTION OF A PREFERRED EMBODIMENT

Figure 1:
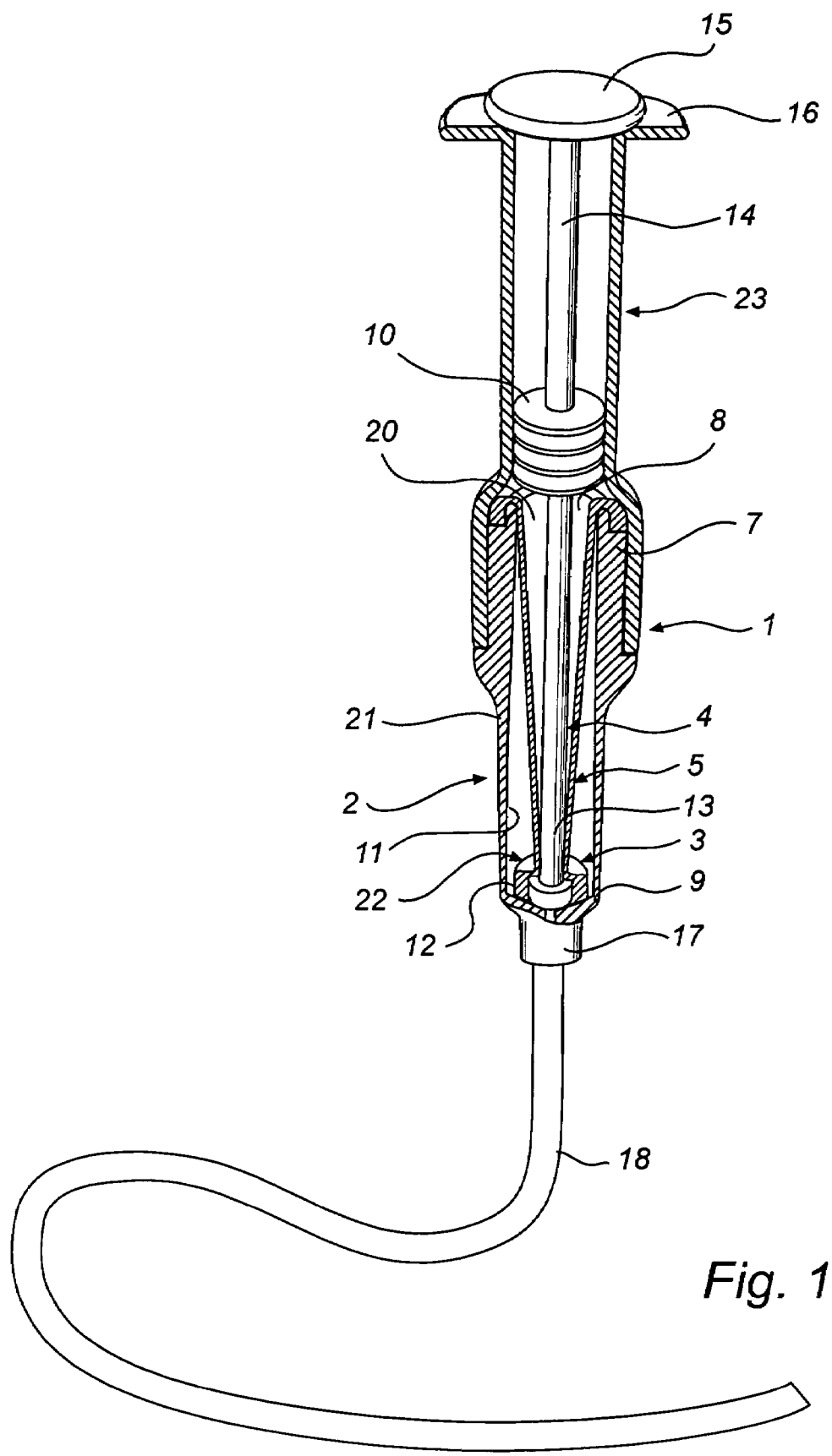
FIG. 1 is a perspective side view, partly in cross-section, of a currently particularly preferred embodiment of a syringe according to the invention in a first starting position.
Figure 2:
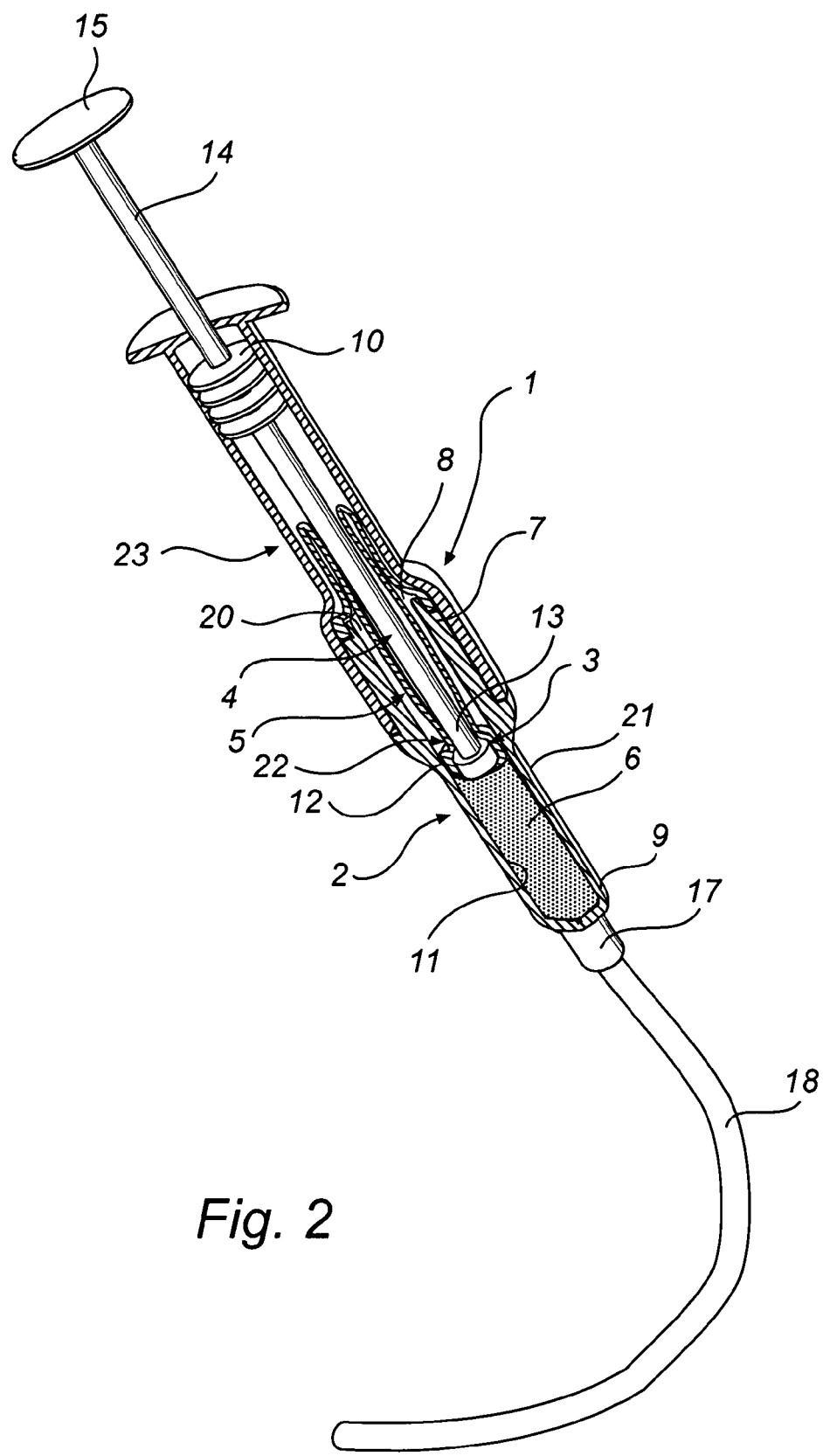
FIG. 2 is a view corresponding to FIG. 1 showing the syringe in a second starting position.

The syringe generally designated 1 in the drawing is, as mentioned above, in the first place intended to be used in contamination-free take-up from process vessels, collecting vessels or the like in order to transfer a medium to another process vessel or the like, transfer of the medium to a laboratory for analysis etc.

However, there is nothing to prevent the syringe according to the invention from being used in other applications, for instance as a conventional sampling or injection syringe in the medical field, such as in medical care. Other conceivable applications are as dosing syringe for controlled dosing of components included in a composition or pharmaceutical preparation, as laboratory syringe etc.

The main components of the syringe 1 are a cylinder 2, a piston portion 3, a piston rod 4 and a sealing means 5.

More specifically, the cylinder 2 is formed as a hollow, substantially straight circular cylinder to take up a liquid medium 6, or a gas, from a collecting vessel or the like (not shown). The cylinder 2 has a first end 7 with a circular opening 8 and a second end 9 with an inlet and outlet part suitably integrated with the cylinder.

The piston portion 3 is also circular and is guided in the cylinder 2 in such a manner that it is movable back and forth in the cylinder between the first and second ends 7, 9 thereof. The piston portion 3 is sealingly guided in the cylinder 2 by sealingly engaging the inside 11 of the cylinder with a seal which, in the embodiment according to FIG. 1, is integrated in the sealing means 5 and has the shape of one or more sealing edges 12 or ridges. The sealing edges 12 are preferably made of the same material as the sealing means 5, which can be a suitable elastomer, such as rubber or silicone, or alternativley some other polymer material.

In the shown embodiment, the piston rod 4 is circular in cross-section and is at its inner end 13 connected to the sealing means 5 which forms a piston portion 3. The piston rod can also be X-shaped in cross-section or have some other cross-section. The piston rod 4 projects from the opening 8 at the first end of the cylinder and has at its outer end 14 a handle 15 which here has the shape of a round disc and suitably is integrated with the piston rod 4. Moreover a sleeve 23 is fastened around the first end of the cylinder 2 and secures the sealing means at the first end of the cylinder 2. The sleeve 23 also guides the flanges 10 of the piston rod to perform a control movement of the piston rod and the piston portion inside the cylinder 2.

For cooperation with the handle 15, the end of the sleeve is formed on its outside with a counter-handle 16 which is suitably integrated with the sleeve. The piston rod 4 is manually actuatable from the outside by the handle 15 and the counterhandle 16 to move the piston portion 3 back and forth in the cylinder 2.

At the second end 9 of the cylinder 2 there is an inlet and outlet part 17 to allow the medium to pass into and out of the cylinder 2. The inlet and outlet part 17 can be designed in various ways; in this case like a connecting nozzle to be connected to a tube 18 from the connecting vessel or the like (not shown). Alternatively, the inlet and outlet part 17 could be designed as a holder or connection for an injection needle or the like.

In the embodiment here illustrated and described, the sealing means 5 is made of an elastic and substantially diffusion-tight material, such as rubber or a suitable plastic, and is flat, or alternatively formed as a bellows, to be able to adjust to the movements of the syringe in a manner that will be described below.

The sealing means 5 is connected to the cylinder 2 by gluing, fusion welding, pressing or some other suitable sealing, to enclose, sealed against contamination or free of contamination, the opening 8 in the first end 7 of the cylinder and also isolate the piston rod 4 extending into the cylinder 2 from the inside 11 of the cylinder in order to prevent contamination of the inside of the cylinder and eliminate the risk that the medium 6 handled in the syringe should be contaminated.

In the shown and described embodiment, in FIGS. 1-4, the sealing means 5 has an upper open end 20, which is sealed and connected, sealed against contamination, to the cylinder 2 in the area of its first end 7, more specifically to the outside 21 of the cylinder, as shown at 25.

At its end 22 opposite to the open end 20, the sealing means 5 is in the current embodiment closed and forms a piston portion which has one or more cylindrical sealing edges which sealingly engage the inside of the cylinder.

Figure 7:
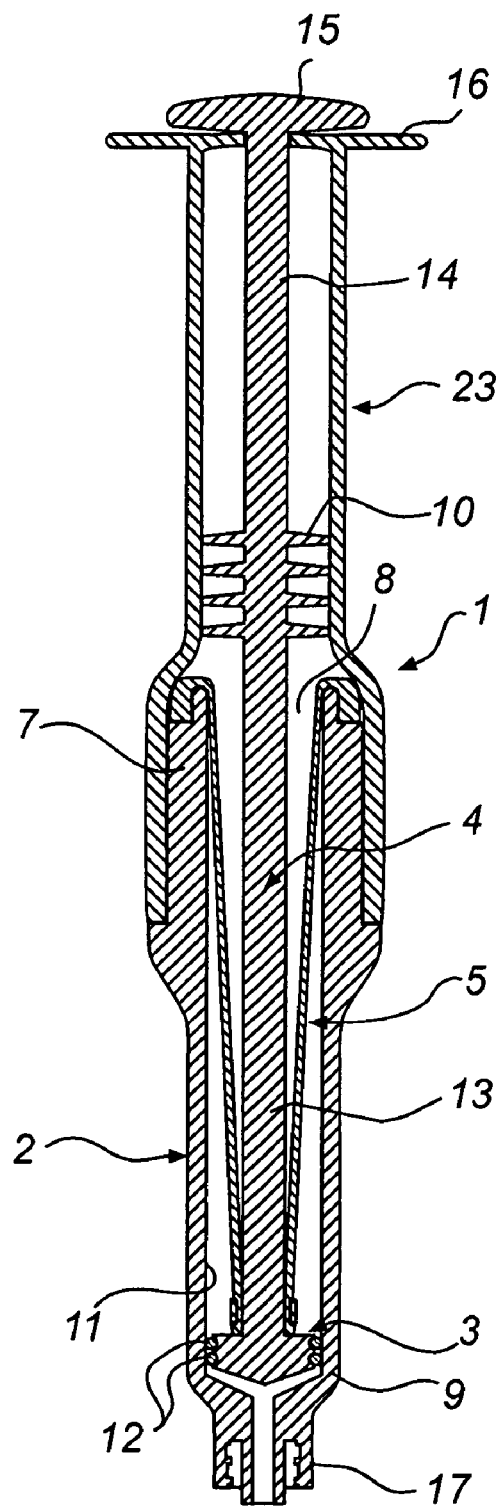
FIG. 7 is a section of an embodiment of the syringe with a piston-like portion of the piston rod.

In an alternative embodiment, according to FIG. 7, also the end 22, opposite to the open end 20, of the sealing means 5 is open and then, suitably in a sealed manner connected directly to the piston rod 4, which is arranged with a, detachable or integrated, piston 3 for sealing against the inside 11 of the cylinder. In this embodiment, the piston can preferably be formed so that, when it is attached to the piston rod 4, also the sealing means 5 is connected, sealed against contamination, to the cylinder 2 and/or the piston 3, which can take place by clamping, barbs, form-fit locking, adhesive or in some other suitable manner.

Irrespective of the design of the syringe 1 and its components 2-23, in the first place the cylinder 2, it is suitably made of a transparent material, for instance an appropriate plastic, and presterilised by a conventional method, such as irradiation or autoclaving.

In a further alternative embodiment, according to FIG. 6, the sleeve 23 has a part connecting to the outside of the first end 7 of the cylinder 2 and a part extending into the first end of the cylinder. In this embodiment, the sleeve 23 is adapted to secure the open end 20 of the sealing means to the opening 8 of the cylinder in a tight-fitting manner, for instance by clamping, barbs, form-fit locking, adhesive or in some other suitable manner. That part of the sleeve 23 which extends into the cylinder 2 can also be used to hold the sealing means 5, apart from the fact that it can be designed as a guide for the piston rod when moving up and down in the cylinder. As a result of this embodiment, the total length of the syringe 1 will be shorter than in the embodiment according to, for instance, FIGS. 1-4.

Figure 3:
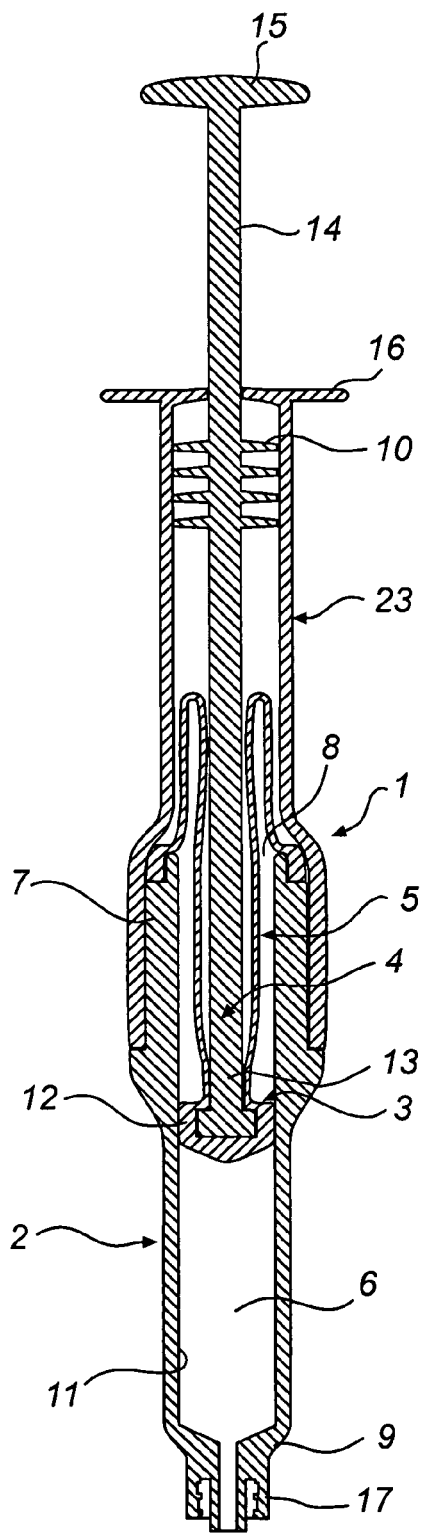
FIG. 3 is a section of the syringe according to the invention in a second starting position, FIG. 4. is a section of the syringe according to the invention in a first starting position.
Figure 4:
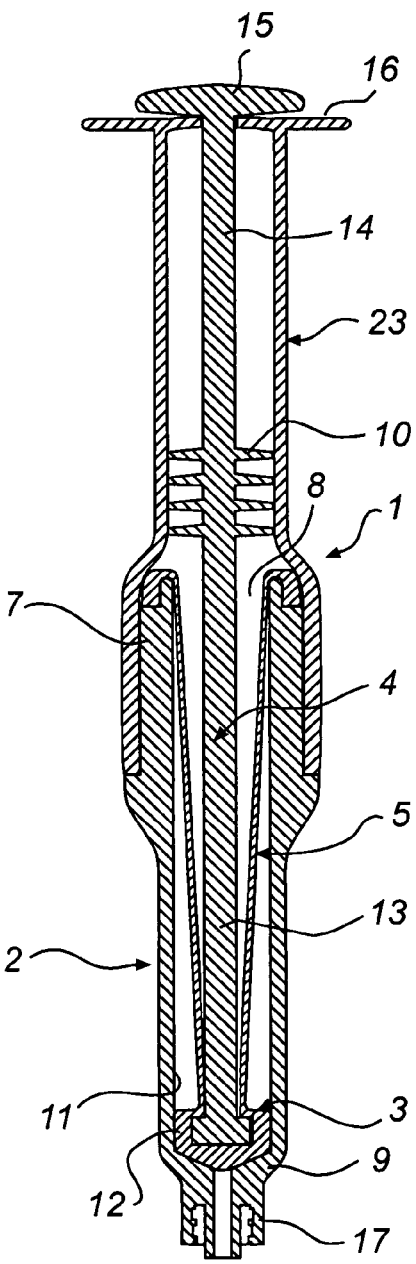

In the syringe 1 according to one of the above embodiments, the sealing means 5 can be formed as a smooth and flexible cylinder or cone, which is open at an upper end 20 and has a sealing piston portion 3, alternatively open, also at the opposite end. That part of the sealing means 5 which interconnects these two ends can be designed in various ways, in order to, for instance, allow good movability of the piston rod 4 of the syringe, for instance as a bellows or in some other suitable shape. When the piston rod 4 of the syringe, in use, is pulled out of the cylinder 2, the sealing means 5 is pressed against the piston rod 4 and, as shown in FIG. 3, the sealing means 5 can be provided to accompany, folded in two, the piston rod 4 out of the opening 8 of the cylinder 2.

It goes without saying that the invention should not be considered limited to the embodiments described above and illustrated in the drawings with the described variants and alternatives, and can be modified further in many different ways within the scope of protection according to the appended claims.

The invention claimed is:

1. A syringe for taking up and discharging a fluid, comprising a cylinder, a piston portion slidably disposed in the cylinder, and an operating means connected to the piston portion for sliding thereof, the operating means projecting from a first end of the cylinder, the cylinder having an inlet and an outlet part for said fluid at a second end, wherein a sealing means is connected in a contamination-free manner to the cylinder in an area of the first end thereof and wherein the sealing means is of such a length that the sealing means may extend into the cylinder to an area of the second end of the cylinder and isolates the inside of the cylinder from the environment.

2. A syringe as claimed in claim 1, wherein said sealing means is arranged to form a seal between the inside of the cylinder and an inner end of the operating means extending into the cylinder.

3. A syringe as claimed in claim 1 or 2, wherein the sealing means is located substantially inside the cylinder.

4. A syringe as claimed in claim 1, wherein the sealing means has an open end into which the inner end of the operating means extends.

5. A syringe as claimed in claim 4, wherein the open end of the sealing means is connected to the first end of the cylinder.

6. A syringe as claimed in claim 1, wherein a guide sleeve is arranged at the first end of the cylinder to guide the operating means.

7. A syringe as claimed in claim 4 or 5, wherein the sealing means forms a piston-like portion at its end opposite to the open end, wherein the piston-like portion is movable by the operating means inside the cylinder, the piston-like portion sealingly engaging the inside of the cylinder.

8. A syringe as claimed in claim 4, wherein the open end of the sealing means is connected to the first end of the cylinder by being turned inside out around the edge of the first end of the cylinder.

9. A syringe as claimed in claim 1, wherein the sealing means is made of an elastic and sealing material.

10. A syringe as claimed in claim 1, wherein said syringe and sealing means are pre-sterilized.

11. The syringe of claim 10, wherein the syringe and sealing means are pre-sterilized by irradiation.

12. A syringe as claimed in claim 1, wherein the opposite end of the sealing means, at the inner end of the operating means, is movable and the open end of the sealing means is held still at the first end of the cylinder.

13. A syringe for taking up and discharging a fluid, comprising a cylinder, a piston portion slidably disposed in the cylinder, and an operating portion connected to the piston portion for sliding thereof, the operating portion projecting from a first end of the cylinder, the cylinder having an inlet and an outlet part for said fluid at a second end, wherein a sealing portion is connected in a contamination-free manner to the cylinder in the area of the first end thereof and wherein the sealing portion maintains the contamination-free connection to the cylinder when the piston portion is disposed at the second end of the cylinder and isolates the inside of the cylinder from the environment.

14. A syringe as claimed in claim 13, wherein said sealing portion is arranged to form a seal between the inside of the cylinder and an inner end of the operating portion extending into the cylinder.

15. A syringe as claimed in claim 13, wherein the sealing portion is located substantially inside the cylinder.

16. A syringe as claimed in claim 13, wherein the sealing portion has an open end into which the inner end of the operating portion extends.

17. A syringe as claimed in claim 16, wherein the open end of the sealing portion is connected to the first end of the cylinder by being turned inside out around an edge of the first end of the cylinder.

18. A syringe as claimed in claim 16, wherein the opposite end of the sealing portion, at the inner end of the operating portion, is movable and the open end of the sealing portion is held still at the first end of the cylinder.

19. A syringe as claimed in claim 1, wherein a first end of the sealing means is connected in a contamination-free manner to the cylinder and wherein a second end of the sealing means is connected to the piston portion.

20. A syringe as claimed in claim 13, wherein a first end of the sealing portion is connected in a contamination-free manner to the cylinder in the area of the first end thereof and wherein a second end of the sealing portion is connected to the piston portion.

* * * * *

UNITED STATES PATENT AND TRADEMARK OFFICE
CERTIFICATE OF CORRECTION

PATENT NO. : 7,597,683 B2
APPLICATION NO. : 11/359482
DATED : October 6, 2009
INVENTOR(S) : Myhrberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 621 days.

Signed and Sealed this

Twenty-eighth Day of September, 2010

David J. Kappos
*Director of the United States Patent and Trademark Office*